United States Patent [19]

Andress

[11] 4,016,092
[45] Apr. 5, 1977

[54] ORGANIC COMPOSITIONS CONTAINING BORATE AND PHOSPHONATE DERIVATIVES AS DETERGENTS

[75] Inventor: Harry J. Andress, Wenonah, N.J.

[73] Assignee: Mobil Oil Corporation, New York, N.Y.

[22] Filed: Mar. 8, 1976

[21] Appl. No.: 664,853

Related U.S. Application Data

[63] Continuation-in-part of Ser. No. 563,240, March 28, 1975, abandoned.

[52] U.S. Cl. .................................. 252/32.5; 44/58; 44/73; 44/DIG. 4; 252/49.6; 252/49.9; 252/75; 252/78.1; 252/78.5; 260/462 R; 260/944; 260/945
[51] Int. Cl.² .................... C10M 1/46; C10M 1/44; C10M 1/54; C07F 5/04
[58] Field of Search .............. 252/32.5, 49.6, 49.9, 252/78, 75, 78.1, 78.5; 44/58, 73, DIG. 4; 260/944, 945, 462 R

[56]         References Cited
         UNITED STATES PATENTS 3,268,450   8/1966   Sims et al. ..................... 252/49.9
3,649,659   3/1972   Otto et al. ..................... 252/32.5 X
3,697,574  10/1972   Piasek et al. ................. 252/49.6 X
3,756,953   9/1973   Piasek et al. ................. 252/49.6

Primary Examiner—Harris A. Pitlick
Attorney, Agent, or Firm—Charles A. Huggett; Raymond W. Barclay; Thomas S. Szatkowski

[57]            ABSTRACT

An alkyl phenol having from about 20 to about 300 carbon atoms, formaldehyde and trishydroxymethylaminomethane are reacted and the resulting product is then reacted with boric acid, dialkyl phosphonate or a diaryl phosphonate to produce the corresponding borate or phosphonate derivatives. These derivatives are particularly useful as detergents in organic media such as lubricating oils, greases, fuels, heat-exchange fluids and transmission fluids.

11 Claims, No Drawings

ORGANIC COMPOSITIONS CONTAINING BORATE AND PHOSPHONATE DERIVATIVES AS DETERGENTS

CROSS REFERENCE TO RELATED APPLICATIONS

This application is a continuation-in-part of co-pending application Ser. No. 563,240 filed Mar. 28, 1975, now abandoned.

BACKGROUND OF THE INVENTION

1. Field of the Invention

This invention relates to novel organic fluid compositions containing minor amounts of borate or phosphonate derivatives useful as detergents, particularly in lubricating oils, greases, fuels, heat exchange fluids and transmission fluids.

2. Description of the Prior Art

British Pat. No. 1,031,130 describes the reaction between a polyolefinic polysuccinic acid anhydride or halide and a hydroxylated amine such as tris(hydroxymethyl)aminomethane (hereinafter referred to as "TMAM"). These products are described as lubricant detergents.

U.S. Pat. No. 3,632,511 describes a two step process involving reaction between an olefin-substituted succinic acylating agent and an alkylene polyamine followed by the reaction mixture with a hydroxylamine, such as TMAM. U.S. Pat. No. 3,576,743 discloses the reaction between the alkenyl-succinic anhydride and the polyhydric alcohol followed by reaction of the resulting reaction product with a hydroxyl amine such as TMAM. In these two U.S. patents, the resulting product is considered to be a mixture of different products. The products are said to have dispersant and rust-resistant properties for lubricants and fuels.

U.S. Pat. No. 3,649,659 describes a metal coordinated complex product obtained by reacting a basic organic nitrogen compound with an aldehyde and a polyalkylphenol and subsequently reacting the product thus formed with a coordinating agent prepared from a metal and an acid. This product is said to have detergent and neutralizing properties in organic fluids, however in use, such metal containing product results in ash formation.

U.S. Pat. No. 3,697,574 discloses boron derivatives of high molecular weight Mannich condensation products. The products of this reference differ from those of the present invention in that the particular amine used herein, namely TMAM, is not shown. The unexpectedly high detergent properties found for the compositions of the present invention are believed to be the result of using the amine TMAM, as will be described hereinafter.

U.S. Pat. Nos. 3,087,936; 3,284,409 and 3,281,428 describe boron-containing additives; U.S. Pat. No. 3,280,034 describes aldehyde derivatives. None of the above described references discloses the present borate or phosphonate derivatives.

SUMMARY OF THE INVENTION

In accordance with the present invention, novel organic fluid compositions are provided, comprising organic media selected from the group consisting of lubricating oils, greases, fuels, heat-exchange fluids and transmission fluids, and a minor amount, sufficient to impart detergent properties thereto, of the product obtained by (a) reacting an alkyl phenol having from about 20 to about 300 carbon atoms, formaldehyde and trishydroxymethylaminomethane and (b) reacting the product produced from (a) with a member selected from the group consisting of boric acid, dialkyl phosphonates and diaryl phosphonates to produce the corresponding borate or phosphonate derivatives.

In carrying out the above described reaction it is essential that the alkyl phenol contain from about 20 to about 300 carbon atoms. If the alkyl phenol containes less than about 20 carbon atoms, the detergent properties of the ultimate borate or phosphonate derivatives, are impaired. If the alkyl phenol contains more than about 300 carbon atoms, the ultimate detergent product becomes unstable and therefore inefficient. The alkyl phenol, formaldehyde and trishydroxymethylaminomethane component of (a) are preferably reacted in equimolar ratios at temperatures from about 50° C to about 200° C.

The borate or phosphonate derivative is produced by reacting about 1 to about 2 moles of boric acid, dialkyl phosphonate or diaryl phosphonate per mole of the product produced from (a); preferably these reactants are reacted in equimolar amounts. Temperatures from about 50° C to about 250° C; preferably 100° C to 200° C are used for this reaction.

The borate or phosphonate derivatives may be employed in minor amounts. For many applications, these derivatives are employed in an amount from about 0.1 to about 25% by weight of the total weight of the composition. Preferred, alkyl phenols include polypropyl alkyl phenols, polybutyl alkyl phenols. Preferred phosphonates include dimethyl phosphonate and diphenyl phosphonate, polyhexyl, polyoctyl, polydecyl, polyhexadecyl, and polyeicosyl phosphonates. The phosphonate derivative may also be prepared by reacting the product of Example 2 with phosphorus trichloride and water. Boron compounds, other than boric acid include trimethyl borate, triethyl borate, tributyl borate, and trioctyl borate.

Of particular significance, in accordance with the present invention, is the ability to improve the detergency of lubricating media which may comprise liquid hydrocarbon oils, in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F to about 6000 SSU at 100° F, and preferably, from about 50 to about 250 SSU at 210° F. These oils may have viscosity indexes varying from below zero to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

It is to be understood, however, that the compositions contemplated herein can also contain other materials. For example, corrosion inhibitors, extreme pressure agents, viscosity index agents, anti-oxidants, anti-wear agents and the like can be used. These materials do not detract from the value of the compositions of this invention, rather these materials serve to impart their customary properties to the particular compositions in which they are incorporated.

Of still further significance, is the detergency improvement of petroleum distillate fuel oils having an initial boiling point from about 75° F to about 135° F and an end boiling point from about 250° F to about 750° F. It should be noted, in this respect, that the term "distillate fuel oils" is not intended to be restricted to straight-run distillate fractions. These distillate fuel oils can be straight-run distillate fuel oils, catalytically or thermally cracked (including hydrocracked) distillate fuel oils, naphthas and the like, with cracked distillate stocks. Moreover, such fuel oils can be treated in accordance with well-known commercial methods, such as acid or caustic treatment, hydrogenation, solvent-refining, clay treatment and the like.

The distillate fuel oils are characterized by their relatively low viscosity, pour point and the like. The principal property which characterizes these hydrocarbons, however, is their distillation range. As hereinbefore indicated, this range will lie between about 75° F and about 750° F. Obviously, the distillation range of each individual fuel oil will cover a narrower boiling range, falling nevertheless within the above-specified limits. Likewise, each fuel oil will boil substantially, continuously throughout its distillation range.

Particularly contemplated among the fuel oils are Nos. 1, 2 and 3 fuel oils, used in heating and as diesel fuel oils, gasoline, turbine oil and jet combustion fuels. The fuel oils generally conform to the specification set forth in ASTM Specification D396-48T. Specifications for diesel fuels are defined in ASTM Specification D975-48T. Typical jet fuels are defined in Military Specification MIL-F-5624B.

The mineral oil heat-exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definitions". Specifications for low-temperature and aircraft fluids are defined in U.S. Government Specification MIL-H-5606A.

DESCRIPTION OF SPECIFIC EMBODIMENTS

The following data and examples serve to illustrate the marked degree in detergency improvement of organic media by employing the aforementioned borate or phosphonate derivatives. It will be understood, however, that it is not intended the invention be limited to the particular compositions disclosed, nor the specific borate or phosphonate derivatives employed as detergents. Various modifications thereof can be employed and will be readily apparent to those skilled in the art.

EXAMPLE 1

A mixture of 2000 grams (2.1 mols.) polypropylene, 200 grams (2.1 mols.) phenol and 75 grams boron trifluoride ethyl etherate was stirred at 90° C for about 14 hours. The mixture was then treated with 150 grams of a 30% solution of ammonium hydroxide by stirring for 2 hours at 100° C. Filtration and topping at reduced pressure gave the final product, a polypropyl alkylated phenol.

EXAMPLE 2

A mixture of 640 grams (0.61 mol) polypropyl phenol of Example 1, 74 grams (0.61 mol) trishydroxymethylaminomethane, and 50 grams (0.61 mol) of formalin solution was gradually heated with stirring to about 170° C over an 8 hour period. Filtration and topping at reduced pressure gave the final product.

EXAMPLE 3

A mixture of 1350 grams (1.3 mols) polypropylphenol of Example 1, 155 grams (1.3 mols) trishydroxymethylaminomethane, and 106 grams (1.3 mols) of formalin solution was gradually heated with stirring to about 185° C over an 8 hour period. The reaction product was cooled to 90° C and 78 grams (1.3 mols) boric acid and 300 grams (4.0 mols) n-butanol were added. The mixture was gradually heated with stirring to about 210° C over a 6 hour period. Filtration and topping at reduced pressure gave the final product.

EXAMPLE 4

A mixture of 271 grams (0.26 mols) polypropylphenol of Example 1, 31 grams (0.26 mols) trishydroxymethylaminoethane and 21 grams (0.26 mols) of formalin solution was gradually heated with stirring to about 180° C over an 8 hour period. The reaction product was cooled to 90° C and 29 grams (0.26 mols) dimethyl phosphonate was added. The mixture was gradually heated with stirring to about 175° C over a 6 hour period. Filtration and topping at reduced pressure gave the final product.

EXAMPLE 5

A mixture of 1100 grams (1.0 mol) polybutylphenol, 94.5 grams (0.5 mols) tetraethylene pentamine, and 82 grams (1.0 mols) of formalin solution was gradually heated with stirring to about 175° C over an 8 hour period. Filtration and topping at reduced pressure gave the final product.

EXAMPLE 6

A mixture of 1100 grams (1.0 mol) polybutylphenol, 52.5 grams (0.5 mol) diethylene triamine, and 82 grams (1.0 mol) of formalin solution was gradually heated with stirring to about 175° C over an 8 hour period. Filtration and topping at reduced pressure gave the final product.

EXAMPLE 7

A mixture of 1100 grams (1.0 mol) polybutylphenol, 94.5 grams (0.5 mol) tetraethylene pentamine, and 82 grams (1.0 mol) of formalin solution was gradually heated with stirring to about 175° C over an 8 hour period. The reaction product was cooled to 70° C and 62 grams (1.0 mol) boric acid and 300 grams (4.0 mols) n-butanol were added. The mixture was gradually heated with stirring to about 215° C over an 8 hour period. Filtration and topping at reduced pressure gave the final product.

EXAMPLE 8

The mixture of 1000 grams (1.0 mol) polypropylphenol of Example 1, 94.5 grams (0.5 mol) tetraethylene pentamine, and 82 grams (1.0 mol) of formalin solution was gradually heated to about 175° C over an 8 hour period. Filtration and topping at reduced pressure gave the final product.

The individual borate and phosphonate derivatives of the foregoing examples were next individually blended in a base fluid comprising a mixture of 80%, by weight, of a solvent-refined paraffinic bright stock mineral oil, 20%, by weight, of a solvent-refined paraffinic distillate mineral oil, 1.3%, by weight, of an overbased magnesium sulfonate, 1.2%, by weight, of zinc dithiophosphate and 1.0%, by weight, of barium dithiophosphate. The base fluid and the same base fluid containing the aforementioned individual additives were next subjected for evaluation in a diesel oil test. This test was developed to produce deposits from the oxidation of lubrication oil under conditions which closely approximate those found in the piston zone of a diesel engine. The test consists of aluminum cylinder heated by radiant energy from an internal heater. The surface temperature of the heater is maintained at 575° F during the test period (140 minutes). The shaft turns slowly (2 RPM) and dips into an oil sump where it picks up a thin film of oil. This thin film is carried into the oxidation zone where heated gases (moist air at 350° F is typically employed, however, nitrogen oxides, sulfur oxides and other mixtures can be used) from oxidation deposits. These deposits can be affected by the detergent as the test cylinder rotates into the sump. The efficiency of the detergent is rated by the color and intensity of the deposit on the shaft at the end of the test. The comparative results obtained, employing this test, are shown in the following Table.

TABLE 1

| DIESEL OIL TEST | | |
|---|---|---|
| Compound | Conc. wt.% | Rating at 140 Minutes |
| Base Fluid | 0 | 62 |
| Base Fluid + Ex. 1 | 3.0 | 64 |
| Base Fluid + Ex. 2 | 3.0 | 74 |
| Base Fluid + Ex. 3 | 3.0 | 91 |
| Base Fluid + Ex. 4 | 3.0 | 79 |
| Base Fluid + Ex. 5 | 3.0 | 65 |
| Base Fluid + Ex. 6 | 3.0 | 62 |
| Base Fluid + Ex. 7 | 3.0 | 69 |
| Base Fluid + Ex. 8 | 3.0 | 67 |

As will be seen from the foregoing comparative data and results, the borate and phosphonate derivatives of the present invention exhibit an ability to impart markedly improved detergent properties to organic compositions. The composition of Examples 3 and 4, representing those products made with the amine TMAM are commercially valuable organic materials having improved detergency properties, as compared with the detergency properties of the base fluid and Examples 1, 2 and 5–8 which are not considered acceptable from a similar standpoint.

Although the present invention has been described with preferred embodiments, it will be understood with various modifications and adaptations thereof may be resorted to without departing from the spirit and scope of the invention as those skilled in the art will readily understand.

I claim:

1. An organic fluid composition comprising an organic medium selected from the group consisting of lubrication oils, greases, distillate fuel oils, mineral oil heat-exchange fluids and petroleum base power transmission fluids, and a minor amount, sufficient to impart detergent properties thereto, of the product obtained by (a) reacting an alkyl phenol having from about 20 to about 300 carbon atoms, formaldehyde and trishydroxymethylaminomethane and (b) reacting the product produced from (a) with a member selected from the group consisting of boric acid, dialkyl phosphonates and diaryl phosphonates in amounts from about 1 to 2 moles per mole of product produced from (a) and at temperatures from about 50° C to about 250° C to produce the corresponding borate or phosphonate derivatives.

2. The composition of claim 1 wherein the alkyl phenol, formaldehyde and trishydroxymethylaminomethane are reacted in equimolar ratios.

3. The composition of claim 1 wherein said borate or phosphonate derivative is present in an amount from about 0.1 to about 25%, by weight of the total weight of the composition.

4. The composition of claim 1 wherein said borate or phosphonate derivative is present in an amount from about 0.1 to about 10%, by weight of the total weight of the composition.

5. The composition of claim 1 wherein the alkyl phenol of (a) is a polypropyl alkyl phenol.

6. The composition of claim 1 wherein the alkyl phenol of (a) is a polybutyl alkyl phenol.

7. The composition of claim 1 wherein the dialkyl phosphonate of (b) is dimethyl phosphonate.

8. The composition of claim 1 wherein the diaryl phosphonate of (b) is diphenyl phosphonate.

9. The product obtained by (a) reacting an alkyl phenol having from about 20 to about 300 carbon atoms, formaldehyde and trishydroxymethylaminomethane and (b) reacting the product produced from (a) with a member selected from the group consisting of boric acid, dialkyl phosphonates and diaryl phosphonates in amounts from about 1 to 2 moles per mole of product produced from (a) and at temperatures from about 50° C to about 250° C to produce the corresponding borate or phosphonate derivatives.

10. The product obtained by (a) reacting a polypropyl alkyl phenol, formaldehyde and trishydroxymethylaminomethane in equimolar ratios and (b) reacting the product produced from (a) with boric acid in equimolar ratios and at temperatures from about 50° C to about 250° C to produce the corresponding borate derivative.

11. The product obtained by (a) reacting a polypropyl alkyl phenol, formaldehyde and trishydroxymethylaminomethane in equimolar ratios and (b) reacting the product produced from (a) with dimethyl phosphonate at equimolar ratios and at temperatures from about 50° C to about 250° C to produce the corresponding phosphonate derivative.

* * * * *